United States Patent
Kobayashi

(10) Patent No.: US 7,754,898 B2
(45) Date of Patent: Jul. 13, 2010

(54) METHOD OF ENANTIOSELECTIVE NUCLEOPHILIC ADDITION REACTION OF ENAMIDE TO IMINE AND SYNTHESIS METHOD OF α-AMINO-γ-KETO ACID ESTER

(75) Inventor: Shu Kobayashi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 853 days.

(21) Appl. No.: 10/587,075

(22) PCT Filed: Jan. 24, 2005

(86) PCT No.: PCT/JP2005/001282

§ 371 (c)(1),
(2), (4) Date: Sep. 29, 2006

(87) PCT Pub. No.: WO2005/070876

PCT Pub. Date: Aug. 4, 2005

(65) Prior Publication Data

US 2007/0161804 A1   Jul. 12, 2007

(30) Foreign Application Priority Data

Jan. 23, 2004   (JP) .............................. 2004-016407

(51) Int. Cl.
*C07D 207/14* (2006.01)
*C07C 229/00* (2006.01)
*C07C 237/00* (2006.01)

(52) U.S. Cl. ................. 548/550; 560/169; 564/152
(58) Field of Classification Search .............. 548/550; 560/169; 564/152
See application file for complete search history.

(56) References Cited

OTHER PUBLICATIONS

Matsubara et al. "Copper(II)-Catalyzed Highly Enantioselective Addition of Enamides to Imines: The Use of Enamides as Nucleophiles in Asymmetric Catalysis" Agewandte Chemie International Edition in English, 2004, vol. 43, No. 13, pp. 1679-1681.*
Li et al. "Enantioselective Oxidative Biaryl Coupling Reactions Catalyzed by 1,5-Diazadecalin Metal Complexes: Efficient Formation of Chiral Functionalized BINOL Derivatives" Journal of Organic Chemistry, 2003, vol. 68, No. 14, pp. 5500-5511.*

\* cited by examiner

*Primary Examiner*—Joseph R Kosack
(74) *Attorney, Agent, or Firm*—Wenderoth, Lind & Ponack, L.L.P.

(57) ABSTRACT

An asymmetric synthesis of amino acid compound that is useful as a starting material or synthetic intermediate for production of medicinal products, agrichemicals, perfumes, functional polymers, etc. There is provided a method of enanthio-selective nucleophilic addition reaction to imine compound being a method of nucleophilic addition reaction of enamide compound accompanied by amino formation to imino group (—CH=N—) of imine compound, characterized in that the reaction is performed in the presence of a chiral copper catalyst. Further, there is provided a novel method of synthesizing an amino acid compound, etc., to which the above is applied.

5 Claims, No Drawings

METHOD OF ENANTIOSELECTIVE NUCLEOPHILIC ADDITION REACTION OF ENAMIDE TO IMINE AND SYNTHESIS METHOD OF α-AMINO-γ-KETO ACID ESTER

TECHNICAL FIELD

The present invention relates to a method of an enantioselective nucleophilic addition reaction of enamide to an imine which enables an asymmetric synthesis of a compound which is useful as a raw material or a synthesis intermediate for producing a pharmaceutical preparation, an agricultural chemical, a fragrance, a functional polymer or the like and, as an application thereof, a synthesis method of an αamino-γ-keto acid ester or the like.

BACKGROUND ART

Conventionally, a method of a nucleophilic addition reaction to an imino group of an imine compound has been studied and, in recent years, this nucleophilic addition reaction has drawn attention as a measure for efficiently and asymmetrically synthesizing an amino acid derivative as a raw material or an intermediate for producing a pharmaceutical preparation, an agricultural chemical, a fragrance, a functional polymer or the like.

Under these circumstances, the present inventors have developed and disclosed a method for synthesizing an N-acylated amino acid derivative by a nucleophilic addition reaction to an N-acylimino ester compound by using a polymer-carrying catalyst (Journal of Combinatorial Chemistry, 2001, Vol. 3, No. 5, 401 to 403) and, further, a method for enantioselectively synthesizing these compounds by using a chiral copper catalyst (Org. Lett. Vol. 4, No. 1, 2002, 143 to 145; J. Am. Chem. Soc. Vol. 125, No. 9, 2003, 2507 to 2515).

However, the nucleophilic addition reaction on which the present inventors have studied is limited to such nucleophilic reactants as a silyl enol ether and an alkyl vinyl ether and, accordingly, a subject to which the nucleophilic addition reaction is applied and such application thereof have inevitably been restricted.

Then, under these circumstances, the present invention has an object of providing a method of an enantioselective nucleophilic addition reaction to an imine compound which enables an asymmetric synthesis of an amino acid compound or the like which is useful as a raw material or a synthesis intermediate for producing a pharmaceutical preparation, an agricultural chemical, a fragrance, a functional polymer or the like and, further, as an application thereof, a novel synthesis method of the amino acid compound or the like.

DISCLOSURE OF THE INVENTION

In order to solve these problems, according to a first aspect of the present invention, there is provided a method of an enantioselective nucleophilic addition reaction of enamide which is a method of a nucleophilic addition reaction of an enamide compound accompanied by generation of an amino group to an imino group (—CH=N—) of an imine compound and which is characterized by allowing the reaction to be performed in the presence of a chiral copper catalyst.

Then, with reference to the above-described method, according to a second aspect of the invention, there is provided the method of the enantioselective nucleophilic addition reaction of enamide which is characterized in that the chiral copper catalyst is constituted by a copper compound which is a salt of an organic or inorganic acid or a complex or composite of the salt, and a chiral diamine ligand and, according to a third aspect of the invention, there is provided the method of the enantioselective nucleophilic addition reaction of enamide which is characterized in that the chiral diamine ligand has an ethylene diamine structure as a portion thereof.

Further, according to a fourth aspect of the invention, with reference to the above-described method, there is provided a method for synthesizing an optically active α-amino-γ-imino acid ester which is characterized in that the imine compound is represented by the following formula (1):

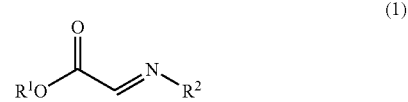

(1)

(wherein $R^1$ represents a hydrocarbon group which may have a substituent; $R^2$ represents an $R^0$—CO— or $R^0$—O—CO— group, wherein $R^0$ represents a hydrocarbon group which may have a substituent); and the enamide compound is represented by the following formula (2):

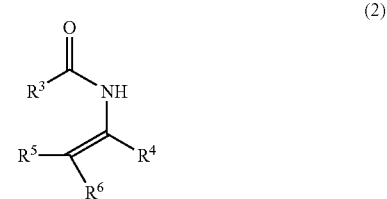

(2)

(wherein $R^3$ represents a hydrocarbon group which may have a substituent or a hydrocarbon group which may have a substituent to be bonded via an oxygen atom; $R^4$ represents a hydrocarbon group which may have a substituent; and $R^5$ and $R^6$ may be same with or different from each other and each represent a hydrogen atom or a hydrocarbon group which may have a substituent, wherein at least one of them represents a hydrogen atom) and generates a compound, namely, an α-amino-γ-imino acid compound, represented by at least one of the following formulae (3):

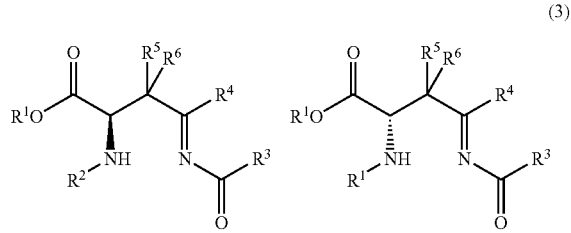

(3)

(wherein $R^1$, $R^2$, $R^3$, $R^4$, $R^5$ and $R^6$ each represent same article as described above).

According to a fifth aspect of the invention, there is provided a method for synthesizing an optically active α-amino-γ-keto acid ester which is characterized in that, after the above-described nucleophilic addition reaction, an acid treatment is performed, to thereby generate a compound represented by at least one of the following formulae (4):

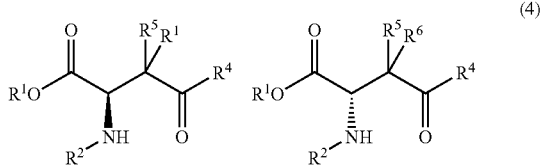

(wherein $R^1$, $R^2$, $R^4$, $R^5$ and $R^6$ each represent same article as described above) and, further, according to a sixth aspect of the invention, there is provided a method for synthesizing an optically active α-amino-γ-keto acid ester which is characterized in that, after the above-described nucleophilic addition reaction, a reduction treatment is performed, to thereby generate a compound represented by at least one of the following formulae (5):

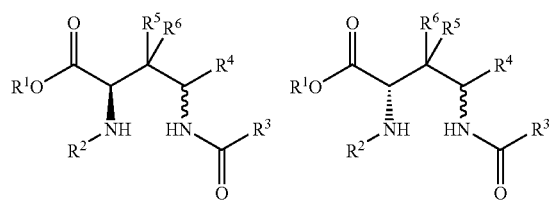

(wherein $R^1$, $R^2$, $R^3$, $R^4$, $R^5$ and $R^6$ each represent same article as described above) and, further, according to a seventh aspect of the invention, there is provided a method for synthesizing optically active γ-lactams which is characterized in that an acyl group of a γ-amino group of the thus-synthesized α, γ-diamino acid ester is removed, to thereby generate a compound represented by at least one of the following formulae (6):

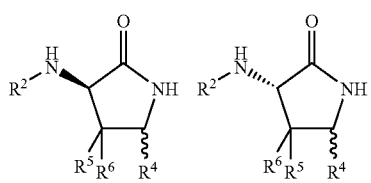

(wherein $R^2$, $R^4$, $R^5$ and $R^6$ each represent same article as described above).

BEST MODE FOR CARRYING OUT THE INVENTION

The present invention has characteristics as described above and is, further, described with reference to embodiments thereof.

In a method of an enantioselective nucleophilic addition reaction of enamide to an imine compound according to the invention, a chiral copper catalyst is used as a catalyst. As for the chiral copper catalyst on this occasion, various types of such chiral catalysts in each of which a copper atom is indispensable for a constitution thereof and to each of which a chiral organic molecular structure is attached are considered. Ordinarily, the chiral copper catalyst is constituted by a copper compound and a chiral organic compound and, more practically, from the standpoint of reaction yield and enantioselectivity, the chiral copper catalyst constituted by a copper compound and a chiral diamine ligand compound is favorably considered.

The copper compound may be selected from among various types of salts, complex salts, organic metal compounds and the like as a monovalent or bivalent copper compound and, among other things, a salt with an organic or inorganic acid, a complex or organic composite of the salt is favorably mentioned. Among these compounds, a salt with a strong acid, for example, a salt of (per)fluoroalkyl sulfonic acid, perchloric acid or sulfonic acid, a complex or an organic composite of the salt is favorably illustrated. For example, $Cu(OTf)_2$, $CuClO_4$, $CuClO_4\text{-}4CH_3CN$ are mentioned.

As for the chiral diamine ligand as a counterpart, an article having an ethylene diamine structure in a molecular constitution as a portion thereof is favorably used. On this occasion, an amino group may contain an imine bond. For example, as representatives, various types represented by the following formulae are illustrated:

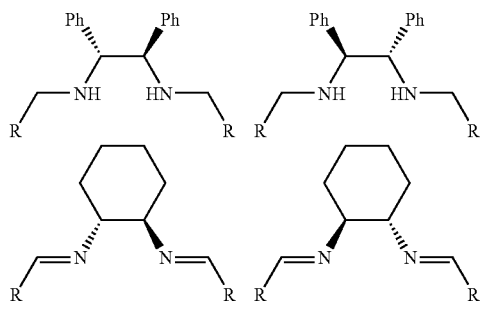

On this occasion, R in the formulae represents a hydrocarbon group which may have a substituent. The hydrocarbon may be any one of various types in a chain state or a cyclic state and may have, as a substituent, a halogen atom, a hydrocarbon group of an alkyl group or the like, an alkoxy group or the like. Further, Ph (phenyl group) in the formulae may have a substituent.

With reference to the chiral copper catalyst as described above according to the invention, a complex may previously be prepared by using a copper compound and a chiral organic molecule and, then, used as a catalyst, or the copper compound and the chiral organic molecule may be mixed with each other in a reaction system and, then, used. As far as a ratio in use as a catalyst is concerned, the copper compound or the complex of the copper compound and the chiral organic molecule is used at a rate of ordinarily from about 0.5 to about 30% by mol against the imine compound.

The imine compound to be used in the reaction may have any one of various types of structures. For example, such imine compound as this is represented by the above-described formula (1). This article has an ester bond portion and reference mark $R^1$ in the formula represents a hydrocarbon group which may have a substituent. The hydrocarbon group may be any one of various types of hydrocarbon groups, for example, a chain or an alicyclic hydrocarbon group, an aromatic hydrocarbon group and mixtures thereof. As for such substituents, so long as they do not interfere with the nucleophilic addition reaction, the hydrocarbon group may appropriately have any one of various types of substituents such as a hydrocarbon group such as an alkyl group, an alkoxy group, a sulfide group, a cyano group, a nitro group, and an ester group.

Further, reference mark $R^3$ may be, as described above, $R^0$—CO— or $R^0$—O—CO—, in which $R^0$ may appropriately be selected from among hydrocarbon groups which each may have a substituent.

The enamide compound as a counterpart can, for example, be represented by the above-described formula (2). As for characteristics thereof, it has an amide bond or a carbamate bond. As for reference marks in the formula, $R^3$ represents a hydrocarbon group which may have a substituent or a hydrocarbon group which may have a substituent to be bonded via an oxygen atom; and $R^5$ and $R^6$ may be same with or different from each other and each represent a hydrogen atom or a hydrocarbon group which may have a substituent, in which at least one of them represents a hydrogen atom.

The hydrocarbon group may be any one of various types of hydrocarbon groups in a same manner as described above, for example, an aliphatic hydrocarbon group, an alicyclic hydrocarbon group, an aromatic hydrocarbon group and mixtures thereof. As for such substituents, various types of substituents such as a hydrocarbon group such as an alkyl group, a halogen atom, an alkoxy group, a sulfide group, a cyano group, a nitro group, and an ester group are appropriately be considered.

Further, as for reference mark $R^3$, a hydrocarbon group which is bonded via an oxygen atom such as —OEt, —O$^t$Bu, or —OBn is appropriately illustrated. As for reference mark $R^4$, an article having a substituent such as a phenyl group, a naphthyl group, or any one of these groups each having a substituent such as a halogen atom, an alkyl group, or an alkoxy group is favorably illustrated.

In the nucleophilic addition reaction of the imine compound to imino (—CH=N—), an appropriate organic solvent, for example, a halogenated hydrocarbon, any one of nitrites, or any one of ethers may be used and, in a reaction temperature, a range of from about −20° C. to about 40° C. can appropriately be adopted. A ratio of the imine compound to the enamide compound to be used in an atmosphere of the air or in an inert atmosphere can appropriately be set to be in the range of from about 0.1 to about 10 in terms of a molar ratio.

In the nucleophilic addition reaction of the enamide compound, when a reaction between the imine compound represented by the above-described formula (1) and the enamide compound represented by the above-described formula (2) is taken as an example, an optically active α-amino-γ-imino acid ester represented by the above-described formula (3) is enantioselectively generated.

By either without isolating or isolating this compound, an acid treatment, for example, an acid treatment by using an aqueous solution of HCl, HBr or the like is performed, to thereby obtain the optically active α-amino-γ-keto acid ester represented by the above-described formula (4) at high yield and with excellent enantioselectivity.

Further, on the other hand, without performing the acid treatment but performing a reduction treatment, the α, γ-diamino acid ester represented by the above-described formula (5) can be obtained at high yield and with excellent enantioselectivity in a same manner as described above. The reduction treatment on this occasion can use, for example, a boron reducing agent compound, any one of other metal hydrides or a metallic hydrogen complex compound. Then, the thus-generated α, γ-diamino acid ester can favorably be converted into any one of γ-lactams as represented by the above-described formula (6) by removing an acyl group on an amino group by an appropriate method (for example, catalytic hydrogen reduction or the like, when the acyl group is a benzyloxycarbonyl group).

Hereinafter, the present invention is described in detail with reference to embodiments. It goes without saying that the present invention is not limited to these embodiments.

EXAMPLES

Example 1

Cu(OTf)$_2$ (7.2 mg, 0.020 mmol) was dried for 2 hours at 100° C. under a vacuum and, then, added with a chiral diamine ligand (10.8 mg, 0.022 mmol) represented by the following formula:

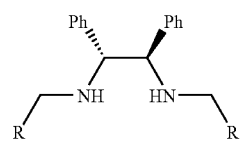

in which R represents a 1-naphthyl group in an argon atmosphere and, thereafter, added with CH$_2$Cl$_2$ (1.5 ml). The resultant light blue solution was stirred for 2 hours or more and, further, added with CH$_2$Cl$_2$ (1.7 ml) and, then, cooled to 0° C.

Next, the resultant mixed solution was added with a CH$_2$Cl$_2$ (0.8 ml) solution of enamide represented by the formula (2) shown in Table 1 and, then, gradually added with a CH$_2$Cl$_2$ (2.0 ml) solution of an imine compound (0.20 mmol) represented by the formula (1) consuming 30 minutes and, thereafter, stirred for 15 minutes at 0° C.

The resultant reaction mixed solution was added with a saturated aqueous solution of NaHCO$_3$, to thereby terminate the reaction. Thereafter, the reaction mixed solution was allowed to have room temperature and subjected to extraction by using CH$_2$Cl$_2$. After the resultant organic phase was rinsed with a saturated saline solution, it was dried by dried magnesium sulfate anhydrous.

After the solvent was evaporated, the resultant residue was dissolved in EtOH (3.0 ml), added with a 48% aqueous HBr solution (0.3 ml) and, then, stirred for 1.5 minute at room temperature.

After the resultant reaction solution was added with an aqueous sodium hydrogen carbonate solution under an ice-cooled condition, it was subjected to extraction by using CH$_2$Cl$_2$ and, then, the resultant organic phase was subjected to a saturation rinse by using a saturated saline solution and, thereafter, dried by using magnesium sulfate anhydrous. Next, the solvent was evaporated therefrom to obtain a crude product. The crude product was purified by using silica gel chromatography.

In Table 1, reaction yield and ee (%) in accordance with the type of enamide are shown. On this occasion, the ee (%) was determined by an HPLC analysis.

TABLE 1

| | Imine compound | | Enamide compound | | | Yield | ee |
|---|---|---|---|---|---|---|---|
| No. | $R^1$ | $R^2$ | $R^3$ | $R^4$ | $R^5$ | (%) | (%) |
| 1 | Et | COC$_{11}$H$_{23}$ | BnO | Ph | H, H | 94 | 93 |
| 2 | Et | COCH$_3$ | BnO | Ph | H, H | 72 | 94 |
| 3 | Bn | COC$_{11}$H$_{23}$ | BnO | Ph | H, H | 89 | 91 |
| 4 | Et | COC$_{11}$H$_{23}$ | Me | Ph | H, H | 83 | 85 |
| 5 | Et | COC$_{11}$H$_{23}$ | BnO | 4-MeO—Ph | H, H | 97 | 90 |
| 6 | Et | COCH$_3$ | BnO | 4-MeO—Ph | H, H | 76 | 92 |

TABLE 1-continued

| | Imine compound | | Enamide compound | | | Yield | ee |
|---|---|---|---|---|---|---|---|
| No. | $R^1$ | $R^2$ | $R^3$ | $R^4$ | $R^5$ | (%) | (%) |
| 7 | Et | $COC_{11}H_{23}$ | BnO | 4-Cl—Ph | H, H | 89 | 90 |
| 8 | Et | $COC_{11}H_{23}$ | BnO | 4-Me—Ph | H, H | 93 | 91 |
| 9 | Et | $COC_{11}H_{23}$ | BnO | 2-naphthyl | H, H | 83 | 88 |
| 10 | Et | $COCH_3$ | BnO | 2-naphthyl | H, H | 76 | 91 |
| 11 | Bn | $COC_{11}H_{23}$ | EtO | Me | H, H | 84 | 83 |

Identification values of products of Nos. 6, 8, 9 and 10 are shown below.

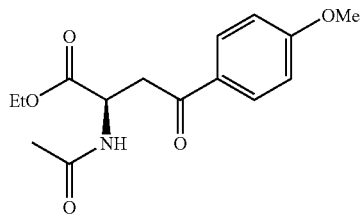

(2R)-Ethyl 2-Acetylamino-4-oxo-4-(4-methoxyphenyl) butyrate: $[\alpha]^{19}{}_D$-108.02 (92% ee, c 1.61, $CHCl_3$); Mp, 117-118° C.; $^1H$ NMR ($CDCl_3$) δ=1.23 (t, 3H, J=7.1 Hz), 2.01 (s, 3H), 3.53 (dd, 1H, J=3.9, 18.0 Hz), 3.70 (dd, 1H, J=3.9 18.0 Hz), 3.88 (s, 3H), 4.21 (q, 2H, J=7.1 Hz), 4.93 (dt, 1H, J=3.9, 7.7 Hz), 6.67 (d, 1H, J=7.7 Hz), 6.94 (d, 2H, J=8.9 Hz), 7.92 (d, 2H, J=8.9 Hz); $^{13}C$ NMR ($CDCl_3$) δ=14.1, 23.2, 40.1, 48.4, 55.6, 61.7, 113.9, 129.1, 130.4, 164.0, 169.9, 171.3, 196.4: IR; (neat) 1602, 1674, 1741 $cm^{-1}$; MS (EI) m/z=293 ($M^+$); HRMS (EI); Exact mass calcd for $C_{15}H_{19}NO_5$ $[M]^+$, 293.1263.

Found 293.1273; HPLC, Daicel Chiralcel AD+AD+AD, hexane/$^i$PrOH=4/1, flow rate=0.75 mL/min: $t_R$=66.5 min (S), $t_R$=70.4 min (R).

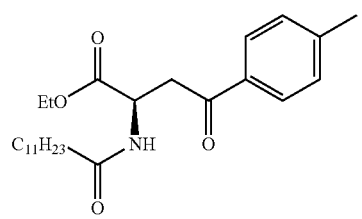

(2R)-2-Dodecanoylamino-4-oxo-4-p-tolyl-butyric acid ethyl ester: $[\alpha]^{27}{}_D$-55.3 (91% ee, c 1.70, $CHCl_3$): Mp. 60-60.5° C.; $^1H$ NMR ($CDCl_3$) δ=0.88 (t, 3H, J=6.6 Hz), 1.15-1.35 (m, 19H), 1.55-1.68 (m, 2H), 2.14-2.27 (m, 2H), 2.41 (s, 3H), 3.56 (dd, 2H, J=4.2, 18.1 Hz), 3.71 (dd, 2H, J=4.1, 18.1 Hz), 4.20 (q, 2H, J=7.1 Hz), 4.96 (dt, 1H, J=4.2, 8.0 Hz), 6.67 (d, 1H, J=8.0 Hz), 7.26 (apparent d, 2H, J=7.8 Hz), 7.83 (apparent d, 2H, J=8.3 Hz); $^{13}C$ NMR ($CDCl_3$) δ=13.9, 14.0, 21.5, 22.5, 25.5, 29.0, 29.2, 29.3, 29.5, 31.8, 36.4, 40.3, 48.1, 61.5, 128.1, 129.3, 133.5, 144.5, 171.2, 172.8, 197.4; IR (neat) 3310, 2925, 2854, 1742, 1682, 1653, 1607, 1523, 1466, 1407, 1367, 1289, 1207, 1182, 1040, 811 $cm^{-1}$; HRMS (FAB); Exact mass calcd for $C_{25}H_{40}NO_4$ $[M+H]^+$, 418.2957. Found 418.2958. Anal. Calcd for $C_{25}H_{39}NO_4$: C, 71.91; H, 9.41; N, 3.35. Found: C, 71.68; H, 9.49; N, 3.72.; HPLC, Daicel Chiralcel AD, hexane/$^i$PrOH=9/1, flow rate=0.5 mL/min: $t_R$=19.8 min (2S), $t_R$=22.7 min (2R).

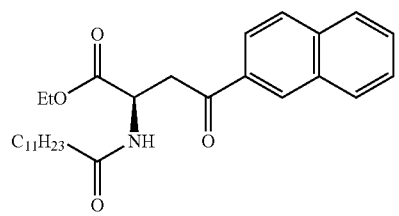

(2R)-2-Dodecanoylamino-4-naphthalen-2-yl-4-oxo-butyric acid ethyl ester: $[\alpha]^{19}{}_D$-45.7 (88% ee, c 0.615, $CHCl_3$); Mp. 75.0-76.0° C.; $^1H$ NMR ($CDCl_3$) δ=0.87 (t, 3H, J=6.8 Hz), 1.10-1.35 (m, 19H), 1.54-1.66 (m, 2H), 2.14-2.30 (m, 2H), 3.75 (dd, 1H, J=4.1, 7.8 Hz), 6.68 (d, 1H, J=4.1, 18.0 Hz), 4.22 (q, 2H, J=7.1 Hz), 5.02 (dt, 1H, J=4.1, 7.8 Hz), 6.68 (d, 1H, J=7.8 Hz), 7.30-7.40 (m, 1H), 7.50-7.65 (m, 2H), 7.85-8.00 (m, 4H); $^{13}C$ NMR ($CDCl_3$) δ=14.0, 14.0, 22.6, 23.5, 29.1, 29.2, 29.2, 29.4, 29.5, 31.8, 36.5, 40.5, 48.3, 61.7, 66.8, 123.4, 126.9, 127.7, 128.0, 128.1, 128.5, 128.6, 128.8, 129.6, 130.2, 132.4, 133.3, 135.8, 171.2, 173.0, 197.9; IR (neat) 3333, 3060, 2922, 2852, 1733, 1684, 1644, 1545, 1468, 1401, 1366, 1230, 1173, 1126, 1047, 815, 749, 668, 566 $cm^{-1}$; HRMS (EI) Exact mass calcd for $C_{28}H_{39}NO_4$ $[M]^+$, 453.2879. Found 453.2885; HPLC, Daicel Chiralcel AD, hexane/$^i$PrOH=19/1, flow rate=1.0 mL/min: $t_R$=29.6 min (S), $t_R$=36.3 min (R).

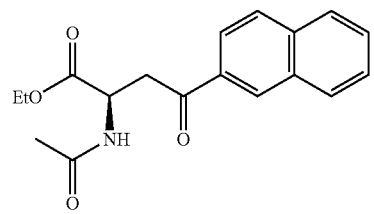

(2R)-2-Acetylamino-4-naphthalen-2-yl-4-oxo-butyric acid ethyl ester: $[\alpha]^{27}{}_D$-81.9 (91% ee, c 0.835, $CHCl_3$); Mp. 94-95° C.; $^1H$ NMR ($CDCl_3$) δ=1.23 (t, 3H, J=7.2 Hz), 2.03 (s, 3H), 3.75 (dd, 2H, J=3.9, 18.1 Hz), 3.87 (dd, 2H, J=4.2, 18.1 Hz), 4.22 (q, 2H, J=7.2 Hz), 5.02 (dt, 1H, J=3.9, 8.0 Hz), 6.79 (d, 1H, J=8.0 Hz), 7.50-7.65 (m, 2H), 7.85-7.90 (m, 2H), 7.92, 8.00 (m, 2H), 8.46 (s, 1H); $^{13}C$ NMR ($CDCl_3$) δ=14.0, 23.0, 40.5, 48.4, 61.6, 123.3, 126.9, 127.7, 128.5, 128.7, 129.5, 130.2, 132.3, 133.2, 135.7, 169.9, 171.1, 197.9; IR (neat) 3289, 3059, 2983, 2935, 1736, 1677, 1541, 1469, 1372, 1281, 1214, 1191, 1124, 1022, 944, 859, 822 $cm^{-1}$; LRMS (FAB) m/z=3.14 ($M+H^+$); Anal. calcd for $C_{19}H_{19}NO_4$; C, 68.99; H, 6.11; N, 4.47. Found: C, 68.89; H, 6.22; N, 4.32.; HPLC, Daicel Chiralcel AD, hexane/$^i$PrOH=4/1, flow rate=1.0 mL/min: $t_R$=13.0 min (2S), $t_R$=15.6 min (2R).

Example 2

In the synthesis of the product of No. 1 in Example 1, a chiral ligand in which R in the above-described formula represents 3,5-di-$^t$BuC$_6$H$_3$ was used.

The yield of the product of No. 1 was 92% and ee (%) was 93.

Example 3

In the synthesis of the product of No. 1 in Example 1, a reaction was performed by using a compound in which $R^1$=Et and $R^2$=OC(CH$_3$)$_3$ as an imine compound and a chiral diamine ligand in which R represents a 2-MeO—C$_6$H$_4$ group in the above-described formula.

The yield of the product was 78% and ee (%) was 87.

Example 4

In the synthesis of the product of No. 11 in Example 1, a chiral diamine ligand in which R represents a 3,5-di$^t$BuC$_6$H$_3$ group in the above-described formula was used.

The yield of the product of No. 11 was 81% and ee (%) was 84.

Example 5

A nucleophilic addition reaction was performed in a same manner as in Example 1 by using an imine compound in which $R^1$=Et, and $R^2$=COC$_{11}$H$_{23}$ in the formula (1) and an enamide compound in which $R^3$=Et, $R^4$=4MeO-Ph, $R^5$=H, $R^6$=Me(E/Z=>99/1<) in the formula (2). The product was isolated without performing an acid treatment using aqueous HBr solution.

The compound described below was obtained with results of yield of 77%, syn/anti of 86/14 and 94% ee (syn).

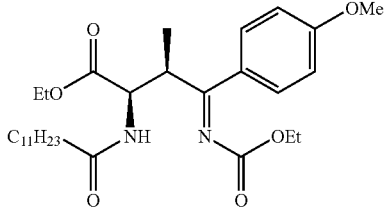

(2R,3R)-2-Dodecanoylamino-4-ethoxycarbonylimino-4-(4-methoxy-phenyl)-3-methyl-butyric acid ethyl ester (syn-lanti=86/14): $^1$H NMR (CDCl$_3$) δ=0.88 (t, 3H, J=6.5 Hz), 1.10-1.40 (m, 2.5H), 1.50-1.75 (m, 2H), 2.10-2.36 (m, 2H), 3.60-3.75 (m, 1H), 3.82 (s, 3H), 4.0-4.3 (m, 4H), 4.75 (dd, 1Hx5/6, J=4.6, 7.9 Hz), 4.94 (dd, 1Hx1/6, J=4.4, 9.2 Hz), 6.26 (d, 1Hx5/6, J=7.9 Hz), 6.76 (d, 1H1/6, J=9.2 Hz), 6.80-7.00 (m, 2H) 7.44 (apparent d, 2H, J=8.6 Hz); HRMS (EI); Exact mass calcd for C$_{29}$H$_{46}$N$_2$O$_6$ [M]$^+$, 518.3356. Found 518.3350; HPLC, Daicel Chiralcel AD+AD, hexane/$^i$PrOH=9/1, flow rate=0.7 mL/min: t$_R$=33.4 min (2S,3R), t$_R$=36.0 min (2S,3S), t$_R$=41.4 min (2R,3S), t$_R$54.4 min(2R,3R).

Example 6

A treatment as described below was performed in place of the acid treatment by using the aqueous HBr solution in Example 1.

Namely, the residue was added with Et$_2$O (7.2 ml) and, then, cooled to −45° C. and, thereafter, added with LiI (133.8 mg, 1.0 mmol) and, subsequently, stirred for 30 minutes. The resultant mixed solution was added with LiAlH (O$^t$Bu)$_3$ (254.3 mg, 1.0 mmol) and, then, stirred for 37 hours at −45° C.

Then, a reaction was terminated by being added with water and, then, further added with a 1N hydrochloric acid. The resultant solution was subjected to extraction by using ether and the resultant organic phase was rinsed with a saturated aqueous solution of sodium hydrogen carbonate and, subsequently, a saturated saline solution and, then, dried by using magnesium sulfate anhydrous.

The compound described below was obtained in an amount of 93.6 mg at a yield of 87%. A ratio of syn/anti was 14/86.

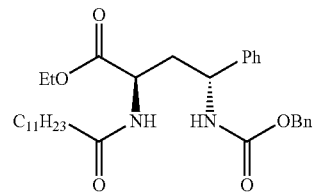

(2R,4R)-4-Benzyloxycarbonylamino-2-dodecanoy-lamino-4-phenyl-butyric acid ethyl ester [α]$^{19}$$_D$-2.0 (92% ee, c 0.465, CHCl$_3$); $^1$H NMR (CDCl$_3$) δ=0.88 (t, 3H, J=6.8 Hz), 1.14-1.38 (m, 19H), 1.48-1.68 (m, 2H), 2.15-2.42 (m, 4H), 4.00-4.20 (m, 2H), 4.54 (brs, 1H), 4.82 (brd, 1H, J=4.9 Hz), 5.05 (d, 1H, J=12.3 Hz), 5.09 (d, 1H, J=12.3 Hz), 5.28 (brs, 1H, 6.19 (brs, 1H), 7.20-7.40 (m, 10H); $^{13}$C NMR (CDCl$_3$) δ=14.0, 14.1, 22.6, 25.4, 29.2, 29.3, 29.3, 29.4, 29.5, 29.6, 31.8, 36.3, 50.1, 61.6, 66.8, 126.5, 127.8, 128.0, 128.0, 128.1, 128.4, 128.5, 128.7, 136.3, 155.7, 171.9, 173.1; IR (neat) 3230, 2925, 2854, 2079, 1715, 1654, 1538, 1455, 1254, 1043, 699, 668, 548 cm$^{-1}$; HRMS (EI); Exact mass calcd for C$_{32}$H$_{46}$N$_2$O$_5$ [M]$^+$, 538.3407. Found 538.3398; Anal. Calcd for C$_{32}$H$_{46}$N$_2$O$_5$: C, 71.34; H, 8.61; N, 5.20. Found: C, 71.11; H, 8.73; N, 5.06; HPLC, Daicel Chiralcel ODH+ODH, hexane/$^i$PrOH=4/1, flow rate=0.2 mL/min: t$_R$=49.0 min (2R), t$_R$=53.9 (2S).

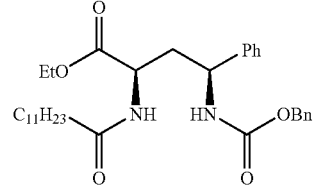

(2R,4S)-4-Benzyloxycarbonylamino-2-dodecanoy-lamino-4-phenyl-butyric acid ethyl ester [α]$^{18}$$_D$-53.6 (92% ee, c0.225, CHCl$_3$); Mp. 98-99° C.; $^1$H NMR (CDCl$_3$) δ=0.88 (t, 3H, J=6.6Hz) 1.18-1.36 (m, 19H), 1.54-1.70 (m, 2H), 4.10-4.26 (m, 2H), 4.62-4.76 (m, 1H), 4.82-4.94 (m, 1H), 5.09 (s, 2H), 5.53 (d, 1H, J=8.3Hz), 6.52 (d, 1H, J=7.6 Hz), 7.20-7.40 (m, 10H); $^{13}$C NMR (CDCl$_3$) δ=14.1, 14.2, 22.7, 25.5, 29.2, 29.3, 29.3, 29.5, 29.6, 31.9, 36.5, 38.6, 49.6, 51.2, 61.8, 67.0, 126.1, 127.7, 128.1, 128.5, 128.8, 136.2, 141.3, 156.0, 172.1, 173.2; IR (neat) 3319, 2923, 2852, 1733, 1691, 1650, 1550, 1454, 1248, 1053 cm$^{-1}$; HRMS (EI): Exact mass calcd for C$_{32}$H$_{46}$N$_2$O$_5$ [M]$^+$, 538.3407. Found 538.3411; Anal. Calcd for C$_{32}$H$_{46}$N$_2$O$_5$: C, 71.34; H, 8.61; N, 5.20. Found; C, 71.12;

H, 8.67; N, 5.09; HPLC, Daicel Chiralcel AD, hexane/$^i$PrOH=9/1, flow rate=0.8 mL/min: t$_R$=10.2 min (2R), t$_R$=16.0 min (2S).

Example 7

γ-lactams were synthesized from the product represented by the following formula in Example 6:

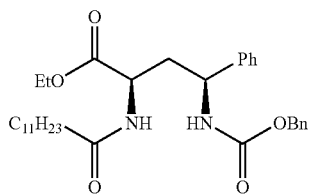

Namely, an AcOEt (2.0 ml) solution of the product (26.5 mg, 0.0492 mmol) was added with 5% Pd/C (10.5 mg, 10% by mol) at room temperature. An argon gas in the atmosphere was replaced with an $H_2$ gas and the resultant mixed solution was stirred for from 15 to 24 hours. Pd/C was filtered out and, then, a filtrate was subjected to vacuum concentration, to thereby obtain a crude product. The thus-obtained crude product was purified by using silica gel chromatography and, as a result, a compound as described below was obtained.

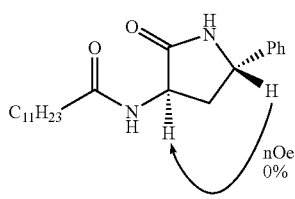

(3R,5S)-Dodecanoic acid (2-oxo-5-phenyl-pyrrolidin-3-yl)-amide $[\alpha]^{30}_D$+13.9 (90% ee, c 0.405, $CHCl_3$); Mp. 118-119° C., $^1$H NMR ($CDCl_3$) δ=0.88 (t, 3H, J=6.6 Hz), 1.20-1.35 (m, 16H), 1.54-1.68 (m, 2H), 2.21 (t, 2H, J=7.6 Hz), 2.43 (dt, 1H, J=9.3, 13.0 Hz), 2.60-2.75 (m, 1H), 4.40-4.54 (m, 1H), 4.82 (d, 1H, J=8.5 Hz), 6.23 (s, 1H), 6.62 (d, 1H, J=14.4 Hz), 7.20-7.40 (m, 5H); $^{13}$C NMR ($CDCl_3$) δ=14.1, 22.7, 25.6, 29.3, 29.4, 29.5, 29.6, 31.9, 36.3, 38.5, 49.5, 55.0, 125.4, 127.9, 129.0, 141.7, 173.9, 175.9; IR (neat) 3295, 3221, 2920, 2850, 1701, 1646, 1556, 1542, 1507, 1458, 1282, 760, 698, $cm^{-1}$; HRMS (FAB); Exact mass calcd for $C_{22}H_{35}N_2O_2$ [M+H]$^+$, 359,2698. Found 359,2713.; HPLC, Daicel Chiralcel ADH, hexane/$^i$PrOH=4/1, flow rate=0.4 mL/min: $t_R$=15.2 min (3S), $t_R$=22.7 min (3R).

Further, a compound as described below was obtained from another product in Example 6 in a same manner as described above.

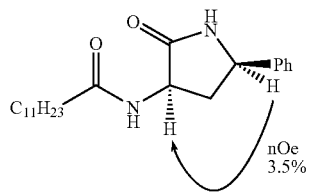

(3R,5R)-Dodecanoic acid (2-oxo-phenyl-pyrrolidin-3-yl)-amide $[\alpha]^{30}_D$−40.8 (91% ee, c 0.345, $CHCl_3$); Mp. 126-127° C.; $^1$H NMR ($CDCl_3$) δ=0.85 (t, 3H, J=6.6 Hz), 1.15-1.36 (m, 16H), 1.55-1.70 (m, 2H), 1.70-1.85 (m, 1H), 2.17-2.27 (m, 2H), 3.10-3.23 (m, 1H), 4.49 (ddd, 1H, J=5.3, 7.9, 11.4 Hz), 4.65 (dd, 1H, J=5.9, 9.7 Hz), 5.91 (s, 1H), 6.08 (d, 1H, J=4.6 Hz), 7.25-7.40 (m, 5H), $^{13}$C NMR ($CDCl_3$) δ=14.1, 22.7, 25.5, 29.2, 29.3, 29.4, 29.6, 31.9, 36.4, 41.0, 51.9, 55.3, 126.0, 128.5, 129.1, 140.5, 173.8, 174.8; IR (neat) 3297, 3249, 2922, 2852, 1699, 1643, 1541, 1457, 1420, 1295, 1242, 1082, 759, 699 $cm^{-1}$; HRMS (FAB); Exact mass calcd for $C_{22}H_{35}N_2O_2$ [M+H]$^+$, 359.2698. Found 359.2702.;

HPLC, Daicel Chiralcel ADH, hexane/$^i$PrOH=4/1, flow rate=0.4 mL/min: $t_R$=13.5 min (3S), $t_R$=18.2 min (3R).

INDUSTRIAL APPLICABILITY

As has been described above in detail, according to the present invention, there is provided a novel method of au enantioselective nucleophilic addition reaction to an imine compound which enables an asymmetric synthesis of an α-amino-γ-keto acid ester, an α, γ-diamino acid ester or the like which is useful as a raw material or a synthesis intermediate for producing a pharmaceutical preparation, an agricultural chemical, a fragrance, a functional polymer or the like. Further, there is provided a novel method for synthesizing any one of optically active γ-lactams as an application thereof.

The invention claimed is:

1. A method of an enantioselective nucleophilic addition reaction of enamide, which comprises reacting an enamide compound and an imine compound in the presence of a chiral copper catalyst to produce a compound with an amino group formed from an imino group (—CH═N—) of the imine compound generated by the nucleophilic addition reaction, the chiral copper catalyst being a bivalent copper compound which is a salt of an organic or inorganic acid or a complex or composite of the salt, and a chiral diamine ligand selected from the group consisting of the compounds represented by the following formulae:

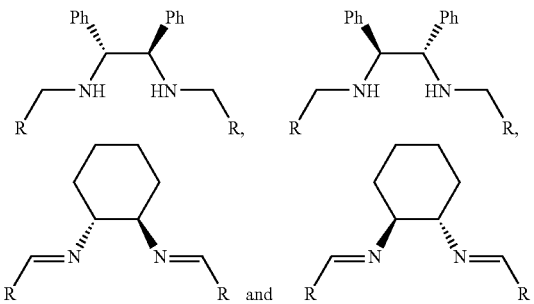

where R represents a hydrocarbon group which may have a substituent.

2. A method for synthesizing an optically active α-amino-γ-imino acid ester, which is the method of the enantioselective nucleophilic addition reaction of enamide according to claim 1, wherein the imine compound is represented by the following formula (1):

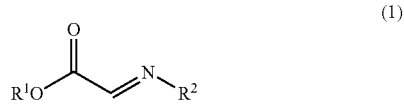

(1)

(wherein $R^1$ represents a hydrocarbon group which may have a substituent; $R^2$ represents an $R^0$—CO— or $R^0$—O—CO— group, wherein $R^0$ represents a hydrocarbon group which may have a substituent); and the enamide compound is represented by the following formula (2):

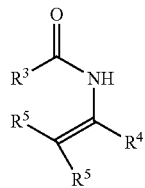
(2)

(wherein $R^3$ represents a hydrocarbon group which may have a substituent or a hydrocarbon group which may have a substituent to be bonded via an oxygen atom; $R^4$ represents a hydrocarbon group which may have a substituent; and $R^5$ and $R^6$ may be same or different from each other and each represents a hydrogen atom or a hydrocarbon group which may have a substituent, wherein at least one of them represents a hydrogen atom), and generates a compound represented by at least one of the following formulae (3):

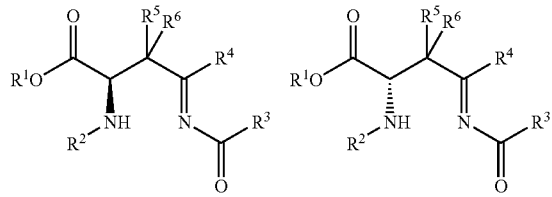
(3)

(wherein $R^1$, $R^2$, $R^3$, $R^4$, $R^5$ and $R^6$ are defined above).

3. A method for synthesizing an optically active α-amino-γ-keto acid ester, which comprises, after the nucleophilic addition reaction according to claim 2, performing an acid treatment to thereby generate a compound represented by at least one of the following formulae (4):

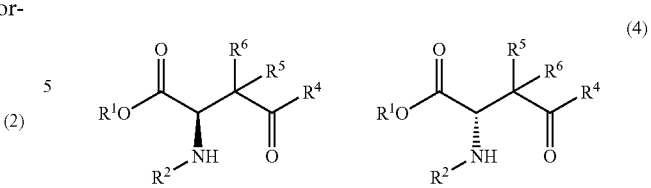
(4)

(wherein $R^1$, $R^2$, $R^4$, $R^5$ and $R^6$ are defined above).

4. A method for synthesizing an optically active α, γ-diamino acid ester, which comprises, after the nucleophilic addition reaction according to claim 2, performing a reduction treatment to thereby generate a compound represented by at least one of the following formulae (5):

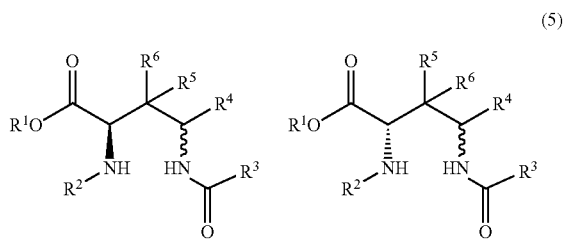
(5)

(wherein $R^1$, $R^2$, $R^3$, $R^4$, $R^5$ and $R^6$ are defined above).

5. A method for synthesizing optically active γ-lactams, which comprises removing an acyl group of a γ-amino group of the optically active α, γ-diamino acid ester synthesized by the method according to claim 4, to thereby generate a compound represented by at least one of the following formulae (6):

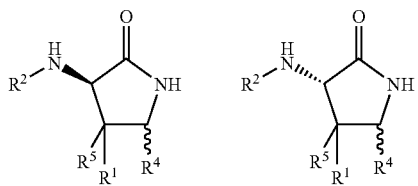
(6)

(wherein $R^2$, $R^4$, $R^5$ and $R^6$ are defined above).

* * * * *